United States Patent [19]

Virgilio et al.

[11] 4,262,127
[45] Apr. 14, 1981

[54] 3-ALKOXY-2-ALKYLISOTHIAZOLIUM SALTS AND THEIR DERIVATIVES

[75] Inventors: Joseph A. Virgilio; Milton Manowitz, both of Wayne; Emanuel Heilweil, Fairfield, all of N.J.

[73] Assignee: Givaudan Corporation, Clifton, N.J.

[21] Appl. No.: 30,181

[22] Filed: Apr. 16, 1979

[51] Int. Cl.$^3$ ............................................. C07D 275/06
[52] U.S. Cl. ..................................... 548/213; 424/270
[58] Field of Search ..................... 260/302 A; 548/213

[56] References Cited

U.S. PATENT DOCUMENTS

| | | | |
|---|---|---|---|
| 3,849,430 | 11/1974 | Lewis et al. ..................... | 260/302 A |
| 3,957,808 | 5/1976 | Miller et al. ..................... | 260/302 A |

OTHER PUBLICATIONS

Fieser, L. et al., "Advanced Organic Chemistry," Reinhold Publishing Corp., New York, pp. 494–495.
Miller, G. et al., "Isothiazole II: 5-chloro-4-isothiazolin-3-ones", Rohm and Haas Co., May 26, 1971.
Horsfall, James G., "Fungicides and their Action," Chronica Botanica Co., Waltham, Mass., 1945; pp. 136–139.

*Primary Examiner*—Nicholas S. Rizzo
*Attorney, Agent, or Firm*—Robert F. Tavares; Thomas Cifelli, Jr.

[57] ABSTRACT

This disclosure relates to a novel class of 3-alkoxy-2-alkylisothiazolium salts. These salts have been found to be useful in controlling the growth of bacteria and fungi. They have also been found to be useful intermediates in the preparation of known antibacterial and antifungal compounds.

19 Claims, No Drawings

3-ALKOXY-2-ALKYLISOTHIAZOLIUM SALTS AND THEIR DERIVATIVES

BACKGROUND OF THE INVENTION

1. Field of the Invention
Antibacterial and Antifungal Compositions
2. Prior Art The 3-alkoxy-2-alkylisothiazolium salts of this invention are novel compounds.

These novel salts can be converted to known 2-alkyl-4-isothiazolin-3-ones as disclosed herein. A number of 2-alkyl-4-isothiazolin-3-ones have been reported in the literature; U.S. Pat. No. 3,761,488; J. Heterocyclic Chem. 8, 571 (1971).

SUMMARY OF THE INVENTION

The novel 3-alkoxy-2-alkylisothiazolium salts of this invention can be represented by the general formula:

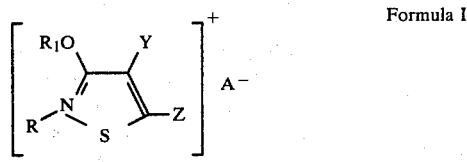

Formula I wherein:
R represents an alkyl or alkenyl group;
$R_1$ represents a alkyl benzyl, alkenyl or alkynyl group
Y and Z represent suitable substituents as defined herein; and
$A^-$ represents a suitable anion.

These novel salts are useful as antibacterial and antifungal agents and find utility in paints, polymer emulsions, paper mills, industrial cooling water, agriculture, soaps, cutting oils, anionic surfactants, adhesives etc. They may be used alone or in admixture with other antimicrobial agents.

The novel 3-alkoxy-2-alkylisothiazolium salts can also be converted to known 2-alkyl-4-isothiazolin-3-ones as illustrated below, wherein B is a suitable base.

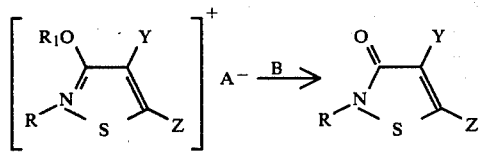

The known 2-alkyl-4-isothiazolin-3-one are valuable antimicrobial agents (U.S. Pat. No. 3,761,488).

The 3-alkoxy-2-alkylisothiazolium salts of this invention are prepared by reacting the corresponding 3-alkoxyisothiazoles with a suitable alkylating agent as illustrated below.

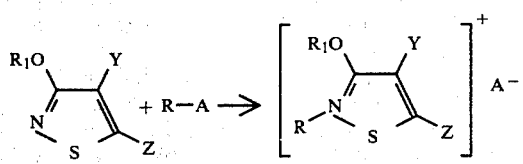

The starting 3-alkoxyisothiazoles can be prepared by methods known in the art [E. Weiler, M. Hausman and G. Miller, J. Hetero, Chem. 14, 725 (1977) and G. Miller and S. Lewis, U.S. Pat. No. 3,957,808].

DESCRIPTION OF THE PREFERRED EMBODIMENTS

The salts of formula I, more particularly the cations thereof, are the essence of this invention. They can be used to control the growth of bacteria and/or fungi and they are useful intermediates in the synthesis of other antibacterial and antifungal agents.

The anionic portion of formula I is not critical and its sole purpose, insofar as is pertinent to this invention, is to neutralize the charge of the cation. The nature of the anion does not materially effect the antimicrobial activity of the cation nor does the anion affect the utility of the salts as intermediates in the preparation of the other antimicrobials. It is not impossible, however, that the anion might play a role in special applications where differences such as stability, solubility or some unique physical property may be significant or where the anion is a special negatively charged species which itself has antimicrobial activity.

In Formula I, the nature of $R_1$ is not critical. It can be any suitable group. For example, alkyl groups (normal or branched) from one to eighteen carbons (including those having cycloalkyl rings, aralkyl groups having seven to eighteen carbons, alkenyl groups from three to eighteen carbons and alkynyl groups of from three to eighteen carbons would be suitable.

Since the preferred method of preparing the starting 3-alkoxyisothiazoles is by alkylating the corresponding 3-hydroxyisothiazoles, the nature of $R_1$ will most probably be determined by the availability and economy of the alkylating agent used. For this reason $R_1$ will preferably be chosen from the group consisting of methyl, ethyl, allyl, methallyl, propargyl and benzyl, with methyl, ethyl, alkyl and benzyl being especially preferred.

The substituents Y and Z can be the same or different. They are preferably chosen from the group consisting of hydrogen or halogen (F, Cl, Br or I with Cl being especially preferred. While variations in Y and Z do appear to have some effect on the level of activity, that effect is one of degree. In all cases tested the level of activity exceeded the level desirable for commercial purposes.

The size of the R group is not critical. Any alkyl or alkenyl group is deemed suitable. The groups may be normal or branched and may be alicyclic or cyclic. As a practical matter, groups having eight carbons or less are preferred (e.g. alkyl groups from methyl to octyl and alkenyl groups from allyl to octenyl). Especially preferred are methyl or ethyl since there are a number of commercially available alkylating agents which are especially suitable for the preparation of the methyl and ethyl analogs.

The anion $A^-$ may be any suitable anion, its sole purpose being to neutralize the charge of the anion, i.e. as a gegen ion. This function could be satisfied by any negatively charged species which would not react with and alter the cation. For example, simple anions such as chloride, bromide, iodide, sulfate, phosphate, carbonate etc. would be suitable.

As a practical matter, however, the anion is normally determined by the alkylating agent used. The most reactive alkylating agents such as dimethyl sulfate, diethyl sulfate, methyl fluorosulfonate, trimethyloxonium fluoroborate, triethyloxonium fluoroborate, trimethyloxonium hexachloroantimonate, n-propyl or n-octyl trifluoromethane sulfonate, trimethyloxonium hexafluorophosphate, methyl trifluoromethane sulfonate, allyl trifluoromethanesulfonate, etc. are preferred, and these provide salts having anions such as fluorosulfonate, methylsulfate, ethylsulfate, trifluoromethanesulfonate, hexachloroantimonate, hexafluorophosphate, tetrafluoroborate, etc. respectively.

The 3-alkoxy-2-alkylisothiazolium salts of this invention are prepared by quaternization of the corresponding 3-alkoxyisothiazole with a suitable alkylating agent. It is preferred to use the most reactive alkylating agents such as dimethyl sulfate, diethyl sulfate, methyl fluorosulfonate, trimethyloxonium fluoroborate, triethyloxonium fluoroborate, trimethyloxonium hexachloroantimonate, n-propyl or n-octyl trifluoromethane sulfonate, trimethyloxonium hexafluorophosphate, methyl trifluoromethane sulfonate trimethyloxonium hexafluorophosphate, methyl trifluoromethanesulfonate, allyl trifluoromethanesulfonate, and the like. Especially preferred are the commercially available agents such as dimethyl sulfate, diethyl sulfate, methyl fluorosulfate, methyl fluorosulfonate, trimethyloxonium fluoroborate, triethyloxonium fluoroborate and the like. Such reagents, known in the art, are preferred since reactions utilizing them occur more rapidly and under milder reaction conditions than those using less reactive alkylating agents such as alkyl halides.

In the preferred process of this invention, the appropriate alkylating agent and isothiazole are brought together and heated to a reaction temperature that is sufficient to effect reaction. The relative amounts of the reactants are not critical and while equimolar amounts are normally preferred, an excess of either reagent is suitable. It is preferred to run the reaction without solvent, but a suitable reaction inert solvent may be used if desired. (The choice of solvent is within the skill of the art, typical examples being methylene chloride, chloroform, ethylene dichloride, ethers such as ethyl ether, dibutyl ether, diphenyl ether, etc.).

The reaction temperature preferred varies with the relative reactivities of the reagents. They normally do not exceed reflux temperature of the reaction mixture. If the reaction temperature required exceeds the boiling point of the reaction mixture, or one of its components, it may be necessary to achieve a higher temperature by running the reaction under pressure in a sealed reaction vessel.

The maximum temperature need only be kept below the thermal decomposition point of the reactants and product involved. Normally, temperatures are not lower than 0° C. nor higher than 250° C. When the more active alkylating agents are used, the preferred range is from about 25° C. to 150° C.

Parameters such as the temperature, reaction time etc. depend upon the relative reactivity of the specific reactants used. The reaction may be complete in as short a time as two minutes, or require as long as forty eight hours.

The salts produced can be purified if necessary by means known in the art. It is usually sufficient to merely wash out excess starting materials with an appropriate solvent such as toluene, benzene, ether, etc. and the like. If further purification is required the salts may be recrystallized from a suitable solvent.

As mentioned, the nature of the anion is immaterial for the applications of this invention with the possible exception certain special applications. If, for any reason, an anion is desired which differs from that normally determined by the alkylating agent, a simple exchange reaction can be run as illustrated below:

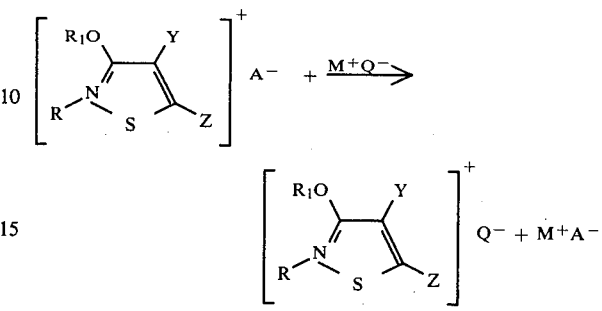

Such an exchange is most thoroughly and efficiently accomplished when $M^+$ is the cationic portion of an ion exchange resin or $M^+$ is chosen such that $M^{30}A^-$ will precipitate from the solution while the resulting 3-alkoxy-2-alkylisothiazolium salt will remain in solution.

While it is preferred to choose $M^+Q^-$ so that either $M^+A^-$ or the new isothiazolium salt produced will precipitate out of solution, the exchange could be effected by creating an equilibrium, removing the solvent and separating the salts by methods known in the art, for example recrystallization techniques. Quite obviously, mixtures of salts wherein the anions are different would also be suitable since such mixtures would have the desired chemical and antimicrobial properties.

The number of inorganic or organic salts that could be used in such an exchange are countless, and it is expected that a chemist skilled in the art could choose a suitable reagent from among these. Such a chemist should, of course, avoid reagents which could be expected to react with the cation, for example an alkali hydroxide, an alkali sulfide etc. Such exchange reactions are, insofar as is pertinent to this invention, merely illustrative of the ease with which a different anion may be introduced if desirable for any reason.

As mentioned, the novel 3-alkoxy-2-alkylisothiazolium salts of this invention provide a convenient starting material for the synthesis of 2-alkyl-4-isothiazolin-3-ones as shown below.

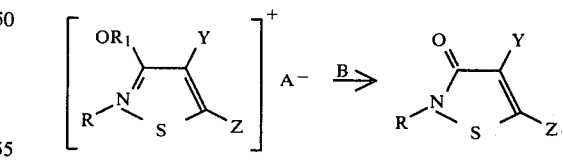

The reaction mechanism for the conversion of the 3-alkoxy-2-alkylisothiazolium salts to the 2-alkyl-4-isothiazolin-3-ones is not clear. Apparently a cleavage of the $R_1$-O bond is involved since a number of reagents, B, are not sources of oxygen.

The reaction requires a suitable base designated by B. By suitable base is meant urea, water, sodium acetate, thiourea, sodium sulfide, sodium hydrosulfide, methyl mercaptan, ethyl xanthate, and the like. The use of a diluent is preferred for purposes of handling and for providing a medium in which the salts will react more readily.

Especially preferred are polar solvents in which the starting salts are somewhat soluble.

Clearly, water is the preferred reagent since the salts are soluble in the reaction medium and the product normally precipitates as formed. While the conversion can be done in water alone, such conversion is slow. Addition of a suitable alkali metal base such as an alkali carbonate, bicarbonate, alkali hydroxides and/or salts of organic acids (alkali acetates etc.) accelerates the reaction and neutralizes the acidic by products.

The conversion is very facile. In an especially preferred process the 3-alkoxy-2-alkylisothiazolium salt of this invention is added to a sodium acetate solution. As the product is formed it normally precipitates from the reaction medium and can be collected by filtration.

Neither temperature nor time appears to be critical. For convenience it is preferred to carry out the reaction at room temperature, but reaction temperatures from below 0° C. to above 100° C. would be suitable.

The reaction time may vary from a few minutes to 12 hrs and would, of course, be dependent on the temperature.

These novel 3-alkoxy-2-alkylisothiazolium salts may be added to such aqueous systems or formulations that are susceptible to bacterial or fungal growth, either undiluted or dissolved in organic solvents such as alcohols, acetone, dimethylformamide and the like. They may be added alone or in combination with other biocides and/or functional compounds such as antioxidants, anticorrosive agents, surfactants, etc.

Concentrations from about 0.05% to above 1.0% are effective. Use of larger concentrations, while feasible, is recommended only for unusual applications. It is preferred to use concentrations from about 0.1% to about 0.5%.

The novel salts may also be used as preservatives for oil in water emulsions. A number of oil in water emulsions are used in industry. For example, in the high speed metal working and textile industries such emulsions are used for their cooling, lubricating, antistatic and anticorrosive properties. Unless adequately protected by an effective preservative, such systems are susceptible to bacterial decomposition producing obnoxious odors and potential health hazards.

In practicing the invention, the compound may be added by directly dissolving it in the concentrated oil which is then diluted with water to form the water oil emulsion, or it may be added to the final emulsion either undiluted or dissolved in a solvent such as dimethylformamide, alcohol, acetone, etc. Similar methods known in the art for adding preservatives to such water and oil emulsions may also be used.

There can be used as little as about 0.005%. Although amounts greater than 0.3% are operable, they are recommended only for unusual applications. It is preferred to use amounts in the range of from about 0.01% to about 0.20% with amounts in the range of about 0.02% to 0.10% being especially preferred.

The novel salts may also be used as cosmetic preservatives. The compounds may be added to the finished cosmetic product directly or dissolved in suitable solvents such as alcohol, acetone, dimethyl formamide and the like. Alternatively the compounds may be dissolved in the oils or other raw materials used in the formula and then formulated in the final product.

In cosmetic preparations, concentrations as low as 0.01% are found to be operable. Concentrations greater than 0.30%, while operable, are recommended only for unusual applications. Concentrations in the range of from about 0.02% to about 0.20% are preferred with concentrations of about 0.05% to 0.10% being especially preferred.

ILLUSTRATION OF PREFERRED EMBODIMENTS

A number of examples are provided herein to illustrate the preferred embodiments of this invention. Included are examples directed to the synthesis of the novel compounds of this invention and examples directed to the utility of these compounds.

The examples provided herein are included for the sole purpose of illustrating the preferred embodiments and should not be construed as limiting. They are intended to embrace any equivalents or obvious extensions which are known or should be known to a person skilled in the art.

Synthesis of the 3-Alkoxy-2-alkylisothiazolium Salts

The following examples illustrate the method of synthesis of the 3-alkoxy-2-alkylisothiazolium salts of this invention.

EXAMPLE I

A. 3-Methoxy-2-methylisothiazolium fluorosulfonate

Methyl fluorosulfonate (6 ml) was added dropwise to 5.4 g (0.046 mol) of 3-methoxyisothiazole (exothermic reaction). After stirring for 30 min., the resulting solid was washed with ether to yield 9.3 g (89%) of 3-methoxy-2-methylisothiazolium fluorosulfonate, mp 120°–123° C.

Analysis: Clcd for $C_5H_8FNO_4S_2$: C, 26.18; H, 3.53; N, 6.11; S, 27.97. Found: C, 26.12; H, 3,47; N, 6.10; S, 27.77.

B. 3-n-Butoxy-2-methylisothiazolium fluorosulfonate 3-n-Butoxyisothiazole (7.2 g, 0.046 mol) and 8 ml of methyl fluorosulfonate were heated to 70° for 1 hr. After cooling, the solid was washed with ether and dried to yield 8.7 g of 3-n-butoxy-2-methylisothiazolium fluorosulfonate a low melting solid. Spectral data (NMR & IR) were consistent with the assigned structure.

C. 2-Methyl-3-n-octoxyisothiazolium fluorosulfonate 3-n-Octoxyisothiazole (5.0 g, 0.023 mol) and 6 ml of methylfluorosulfonate were heated to 70° for 1 hr. After cooling, the solid was washed with ether to yield 6.4 g of 2-methyl-3-n-octyloxyisothiazolium fluorosulfonate, mp 39°–41°. Spectral data (NMR & IR) were consistent with the assigned structure.

D. 3-Alloxy-2-methylisothiazolium fluorosulfonate

3-Allyloxyisothiazole (4.0 g, 0.028 mol) and 5 ml methyl fluorosulfonate were heated at 60° for 45 min. After cooling, the solid was washed with ether to yield 6.5 g (89%) of 3-allyloxy-2-methylisothiazolium fluorosulfonate, mp 50°–53°. Spectral data (NMR & IR) were consistent with the assigned structure.

E. 3-Ethoxy-2-methylisothiazolium fluorosulfonate

3-Ethoxyisothiazole (2.0 g, 0.015 ml) and 2 ml of methyl fluorosulfonate were heated at 50° for 1 hr. The solid was washed with ether to yield 1.9 g (50%) of 3-ethoxy-2-methylisothiazolium fluorosulfonate, mp 65°–68°. Spectral data (NMR & IR) were consistent with the assigned structure.

F. 4-Bromo-3-methoxy-2-methylisothiazolium fluorosulfonate

4-Bromo-3-methoxyisothiazole (8.0 g, 0.041 mol) and 10 ml of methyl fluorosulfonate were heated at 90° for 45 min. After cooling, the solid was washed with ether to yield 10.3 g (81%) of 4-bromo-3-methoxy-2-methylisothiazolium fluorosulfonate, mp 180°–182° C.

Analysis: Clcd for $C_5H_6BrFNO_4S_2$: C, 19.51; H, 2.27; Br, 25.93; N, 4.54; S, 20.80. Found: C, 19.15; H, 2.64; Br, 24.19; N, 4.60; S, 22.01.

G. 4-Chloro-3-methoxy-2-methylisothiazolium fluorosulfonate

Procedure F can be followed using 0.41 mol. of 4-chloro-3-methoxyisothiazole in place of the 4-bromo analog.

H. 3-Benzyloxy-2-methylisothiazolium fluorosulfonate

3-Benzyloxyisothiazole (3.0 g, 0.016 mol) and 5 ml of methyl fluorosulfonate were heated at 60° for 30 min. After cooling, the solid was washed with ether to yield 4.3 g (90%) of 3-benzyloxy-2-methylisothiazolium fluorosulfonate, mp 75°–78° C. (d).

Analysis: Clcd for $C_{11}H_{12}FNO_4S_2$: C, 43.27; H, 3.96; N, 4.59; S, 21.00. Found: C, 43.16; H, 4.12; N, 4.52; S, 20.79.

I. 4,5-Dichloro-3-methoxy-2-methylisothiazolium fluorosulfonate

The starting material (4,5-dichloro-3-methoxyisothiazole) is prepared as follows:

To a suspension of 48.7 g (0.158 mol) of dimethyl dithiodipropionimidate hydrochloride in 400 ml of ethyl acetate at 20°–25° C. was added 84 g of chlorine over 2 hrs. After stirring for 2 hrs, the ethyl acetate was removed on a rotary evaporator. Ether (400 ml) was added to the residue and the solution washed with 300 ml of 10% $K_2CO_3$ solution. The ether was dried ($MgSO_4$), filtered and concentrated. The brown oil was distilled to yield 25.5 g of material, bp 90°–98° C. (15 mm). NMR (proton and $^{13}C$) indicated the material to be a mixture of 4,5-dichloro-3-methoxyisothiazole (40%) and 60% 4-chloro-3-methoxyisothiazole. Fractional recrystallization from hexane (dry ice/acetone) yielded pure 4,5-dichloro-3-methoxyisothiazole, mp 46°–48°.

The 4,5-dichloro-3-methoxy-2-methylisothiazolium fluorosulfonate can then be prepared according to the method of Example I-A by alkylating the 4,5-dichloro-3-methoxyisothiazole prepared above.

J. Preparation of higher alkylated products

In a like manner the higher 3-alkyl analogs can be prepared according to the procedure of Example I-A except that a higher alkylating agent is ued in place of methyl fluorosulfonate, e.g.

(a) Alkylation with n-propyl trifluoromethane sulfonate provides the 2-propyl analog.

(b) Alkylation with n-octyl trifluoromethane sulfonate provides the n-octyl analog.

(c) Alkylation with allyl trifluoromethane sulfonate provides the allyl analog.

Synthesis of 2-alkyl-4-isothiazolin-3-ones

The following illustrates the use of 3-alkoxy-2-alkylisothiazolium salts as intermediates in the synthesis of 2-alkyl-4-isothiazolium-3-ones.

EXAMPLE II

2-Methyl-4-isothiazolin-3-one (a) 3-Methoxy-2-methylisothiazolium fluorosulfonate (6.9 g, 0.030 mol) was added to a saturated NaOAc solution at 40° C. After stirring for 1 hr., the mixture was extracted with 3×100 ml of ether. The extracts were dried ($MgSO_4$) filtered and concentrated. Distillation yield 1.5 g (43%) of product, bp 80° (0.2 mm).

(b) 3-Methoxy-2-methylisothiazolium fluorosulfonate (6.9 g, 0.030 ml) was dissolved in 100 ml of methanol (anhydrous). Thiourea (3.0 g) was added and the mixture was stirred overnight. The methanol was removed on a rotary evaporator and the residue dissolved in 100 ml of $CH_2Cl_2$. The $CH_2Cl_2$ was washed with 100 ml of saturated NaCl solution, dried ($MgSO_4$), filtered and concentrated. Distillation yield 1.0 g (29%) of product.

ILLUSTRATION OF UTILITY

The biocidally active 3-alkoxy-2-alkylisothiazolium salts are suitable for the control of microorganisms in a variety of systems. The following examples are provided to illustrate the utility of the compounds of this invention.

EXAMPLE III

Illustration of General Antimicrobial Activity

Antibacterial and antifungal activity were evaluated by a 5 fold serial dilution test in agar. In this test, compounds were prepared as 6% solutions in dimethylformamide or ethanol. The 6% solution was then 5-fold serially diluted in test tubes to give the desired concentrations when mixed with agar and poured into sterile Petri dishes. Tryptone glucose extract agar was used for the bacterial testing: mildew glucose agar for the fungal testing. The bacterial plates were spot inoculated with 24 hour nutrient broth cultures and incubated at 37° C. for 48 hours. The fungal plates were spot inoculated with spore suspensions and incubated at 28° C. for seven days. At the end of the incubation periods, all plates were examined for growth. The minimum inhibitory concentration (MIC) for each organism is expressed in Table I. In the ranges presented, growth is observed only at the lower concentration.

| Activity | Growth @ | No Growth @ |
|---|---|---|
| 0 | >1920 μg/ml | |
| 1 | 384 μg/ml | 1920 μg/ml |
| 2 | 76 μg/ml | 384 μg/ml |
| 3 | 15 μg/ml | 76 μg/ml |
| 4 | 3 μg/ml | 15 μg/ml |
| 5 | 0.6 μg/ml | 3 μg/ml |
| 6 | 0.12 μg/ml | 0.6 μg/ml |
| 7 | .03 μg/ml | .12 μg/ml |
| 8 | | <.03 μg/ml |

The organisms tested are:

| Bacteria | Fungi |
|---|---|
| $B_1$ S. aureus | $F_1$ A. niger |
| $B_2$ E. coli | $F_2$ A. oryzae |
| $B_3$ P. aeruginosa | $F_3$ P. piscarium |
| $B_4$ P. vulgaris | $F_4$ A. pullulans |

TABLE I

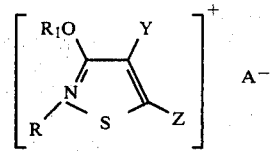

| | | | | | | Minimum Inhibitory Concentration Range (μg/ml) | | | | | | | | | |
|---|---|---|---|---|---|---|---|---|---|---|---|---|---|---|---|
| | | | | | | Bacteria | | | | | Fungi | | | | |
| No. | $R_1$ | R | Y | Z | $A^-$ | $B_1$ | $B_2$ | $B_3$ | $B_4$ | $B_5$ | $F_1$ | $F_2$ | $F_3$ | $F_4$ | |
| 1 | $CH_3$ | $CH_3$ | H | H | $O_3SF$ | 0 | 1 | 1 | 2 | 2 | 0 | 1 | 1 | 1 | |
| 2 | n-Butyl | $CH_3$ | H | H | $O_3SF$ | 3 | 2 | 1 | 3 | 3 | 3 | 3 | 4 | 4 | |
| 3 | Allyl | $CH_3$ | H | H | $O_3SF$ | 1 | 2 | 2 | 2 | 2 | 1 | 1 | 2 | 2 | |
| 4 | $CH_3$ | $CH_3$ | Br | H | $O_3SF$ | 3 | 3 | 3 | 4 | 4 | 2 | 2 | 2 | 2 | |
| 5 | $\phi CH_2$ | $CH_3$ | H | H | $O_3SF$ | 2 | 3 | 3 | 3 | 3 | 3 | 3 | 4 | 3 | |
| 6 | n-Octyl | $CH_3$ | H | H | $O_3SF$ | 3 | 2 | 1 | 3 | 3 | 3 | 3 | 4 | 4 | |
| 7 | $CH_3$ | $CH_3$ | Cl | Cl | $O_3SOMe$ | 5 | 5 | 4 | 5 | 5 | 6 | 6 | 6 | 8 | |

Illustration of Specific Applications

EXAMPLE IV

The utility of the novel compounds of this invention in water and oil emulsions is illustrated below using a commercially available cutting oil.

In running these tests, two-fold serial dilutions of 6% solutions of the compound in dimethylformamide was added to 3.3% cutting oil emulsions. The emulsions were prepared by diluting with water a commercially available cutting oil concentrate. The emulsions were inoculated with a culture of Pseudomonas aeruginosa and incubated at 28° C. on a rotary shaker. At weekly intervals, the emulsions were examined for bacteria by conventional streakplate methods. The emulsions were then reinoculated with Pseudomonas aeruginosa and reincubated.

Table II shows the concentrations required to prevent microbial growth over a four week period in emulsions prepared from a commercially available cutting oil (Kutwell 30). No growth was observed at the concentrations (micrograms per milliliter) given.

TABLE II

| | Incubation Period (Weeks) | | | |
|---|---|---|---|---|
| | 1 | 2 | 3 | 4 |
| $CH_2=CHCH_2O$ ... $CH_3$-N-S-$O_3SF$ | <32 | <32 | 32 | 32 |
| MeO ... $CH_3$-N-S-$O_3SF$ | 32 | 64 | 64 | 64 |
| $\phi CH_2O$ ... $CH_3$-N-S-$O_3SF$ | <32 | <32 | <32 | <32 |
|  | <32 | 32 | 32 | 32 |

We claim:

1. A compound of the formula:

$$\begin{bmatrix} R_1O & & Y \\ & \diagdown & \diagup \\ & N^+ & \\ R \diagup & \diagdown S \diagup & \diagdown Z \end{bmatrix} A^-$$

wherein:
 $R_1$ is chosen from the group consisting of $C_1$ to $C_8$ straight or branch chain alkyl, benzyl, propargyl, allyl and methallyl;
 R is $C_1$ to $C_8$ alkyl or alkenyl
 Y is selected from the group consisting of hydrogen, chlorine and bromine;
 Z is selected from the group consisting of hydrogen or chlorine;
 $A^-$ is a counter ion.

2. A compound according to claim 1 wherein R is methyl, ethyl, propyl, butyl, pentyl, hexyl, heptyl, octyl or allyl.

3. A compound according to claim 2 wherein $R_1$ is methyl, ethyl, allyl or benzyl.

4. A compound according to claim 3 wherein R is methyl or ethyl.

5. A compound of claim 2 wherein Y and Z are hydrogen.

6. A compound of claim 5 wherein R is methyl or ethyl.

7. A compound of claim 6 wherein $R_1$ is methyl, ethyl, allyl or benzyl.

8. A compound of claim 7 wherein $R_1$ and R are methyl.

9. A compound of claim 2 wherein Y and Z are chlorine.

10. A compound of claim 9 wherein R is methyl or ethyl.

11. A compound of claim 10 wherein $R_1$ is methyl, ethyl, allyl or benzyl.

12. A compound of claim 11 wherein $R_1$ and R are methyl.

13. A compound of claim 2 wherein Y is chlorine or bromine and Z is hydrogen.

14. A compound of claim 13 wherein R is methyl or ethyl and $R_1$ is methyl, ethyl, allyl or benzyl.

15. A compound of claim 14 wherein $R_1$ and R are methyl.

16. A process for preparing a 4-isothiazolin-3-one of the formula:

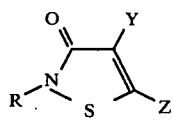

from a 3-alkoxy-2-alkyl isothiazolium salt of the formula:

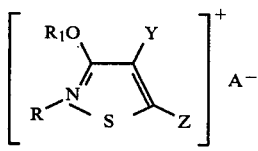

wherein:
R is alkyl or alkenyl;
$R_1$ is $C_1$ to $C_8$ alkyl, benzyl, propargyl, allyl and methallyl
Y is hydrogen chlorine or bromine
Z is hydrogen or chlorine
$A^-$ is a counter ion;
which comprises reacting the salt in the presence of a suitable base.

17. The process of claim 16 wherein the 3-alkoxy-2-alkylisothiazolium salt is reacted with water.

18. The process of claim 16 wherein:
$R_1$ is methyl, ethyl, allyl or benzyl
R is methyl, ethyl, propyl, butyl, pentyl, hexyl, heptyl, octyl or allyl;
Y is hydrogen or chlorine
Z is hydrogen or chlorine
$A^-$ is fluorosulfonate, methylsulfate, hexachloroantimonate, trifluoromethanesulfonate, hexafluorophosphate, tetrafluoroborate, or ethyl sulfate;
and the salt is reacted with water in the presence of an alkali salt of an organic acid, an alkali carbonate, an alkali bicarbonate or an alkali hydroxide.

19. The process of claim 18 wherein
$R_1$ is methyl or ethyl
R is methyl or ethyl and the base is sodium or potassium acetate.

* * * * *